United States Patent [19]
Powers

[11] Patent Number: 4,503,864
[45] Date of Patent: Mar. 12, 1985

[54] URINE SPECIMEN COLLECTION APPARATUS WITH A SEPARABLE COMPARTMENT

[76] Inventor: Jerry G. Powers, 1621 Post Dr., Omaha, Nebr. 68114

[21] Appl. No.: 428,942

[22] Filed: Sep. 30, 1982

[51] Int. Cl.³ .............................................. A61M 1/00
[52] U.S. Cl. .................................. 128/760; 604/317; 73/863.51
[58] Field of Search ............... 128/760, 762, 766, 767, 128/772; 604/317, 318, 327; 73/864.5–864.55, 864.57, 864.64, 864.91, 863.51, 863.52; 422/61, 102; 4/144.1–144.4, 301, 661; 206/569, 570, 363, 602; 220/20; 137/573, 576

[56] References Cited

U.S. PATENT DOCUMENTS

| | | | |
|---|---|---|---|
| 3,640,267 | 2/1972 | Hartig et al. | 128/766 |
| 3,859,671 | 1/1975 | Tomasello | 128/762 |
| 4,265,243 | 5/1981 | Taylor | 128/760 |

Primary Examiner—C. Fred Rosenbaum
Attorney, Agent, or Firm—Schwartz, Jeffery, Schwaab, Mack, Blumenthal & Koch

[57] ABSTRACT

The present invention includes a tray having an inlet, a closed specimen collection container, a closed waste collection container, and a canal connecting the inlet to the waste collection container and the specimen collection container. Structure is provided on the tray whereby the specimen container can be removed from the tray for processing the collected specimen.

8 Claims, 4 Drawing Figures

1

URINE SPECIMEN COLLECTION APPARATUS WITH A SEPARABLE COMPARTMENT

BACKGROUND OF THE INVENTION

1. Field of the Invention

This invention relates to urethral catheterization apparatus for collecting a specimen of urine from a patient.

2. Discussion of Related Art

It is often necessary to obtain a urine specimen from a patient by urethral catheterization. A conventional closed system now used includes a bag collection method in which a bag must be opened and connected to the catheter. After collection, the bag must be opened again to depose of the collect urine, which can be slow and messy process. Alternately, an open method can be employed. This method uses a urethral catheterization tray in which urine is collected in an open collection basin. The basin tends to spill the drained contents upon the bed of the patient. Both of these conventional sytems share the deficiency that the sample collected is exposed to airborne contaminants and thus the specimen may possibly be contaminated producing inaccurate urinalysis.

SUMMARY OF THE PRESENT INVENTION

One object of the present invention is to provide a system of urethral catheterization for collecting a urine specimen which is a closed system free of airborne contamination.

Another object of the present invention is provide a system of urethral catheterization for collecting a urine sample in which the sample collected can be easily removed and sealed and the waste urine can be disposed of easily without any mess.

Yet another object of the present invention is to provide a urethral catheterization system for collecting a urine sample in which the user can exercise control over the collection of urine entering the apparatus so as to collect a specimen only during midstream.

An even further object of the present invention is to provide a urethral catheterization apparatus for collecting a urine sample in which the entire apparatus can be supplied in an aseptic condition and the used components can easily and neatly be disposed of after use.

In accordance with the above and other objects, the present invention includes a tray having an inlet, a closed specimen collection container, a closed waste collection container, and a canal connecting the inlet to the waste collection container and the specimen collection container. Structure is provided on the tray whereby the specimen container can be removed from the tray for processing the collected specimen.

The apparatus also includes structure for sealing the portion of the specimen container connected to the canal after the specimen container has been removed from the tray.

The apparatus can also include a connector which is attached to the tray and adapted for connection to a catheter.

The canal is formed of a drainage canal which leads directly from the inlet to the waste container, and a specimen canal which branches off of the drainage canal and connects to the specimen container. The drainage canal can be formed with a tortuous path prior to the drainage canal branch in order to inhibit the entry of bacteria into the specimen container. Also, the drainage canal can be formed with a curved portion after the specimen canal branch so that the direction of flow can be controlled to increase or decrease the resistance of the flow into the waste container so as fill the specimen container when desired.

BRIEF DESCRIPTION OF THE DRAWINGS

The above and other objects of the present invention will become more readily apparent as the invention is more clearly set forth in the detailed description to follow, reference being had to the accompanying drawings in which like reference numerals represent like parts throughout, and in which.

DETAILED DESCRIPTION OF PREFERRED EMBODIMENTS

Figure 1:
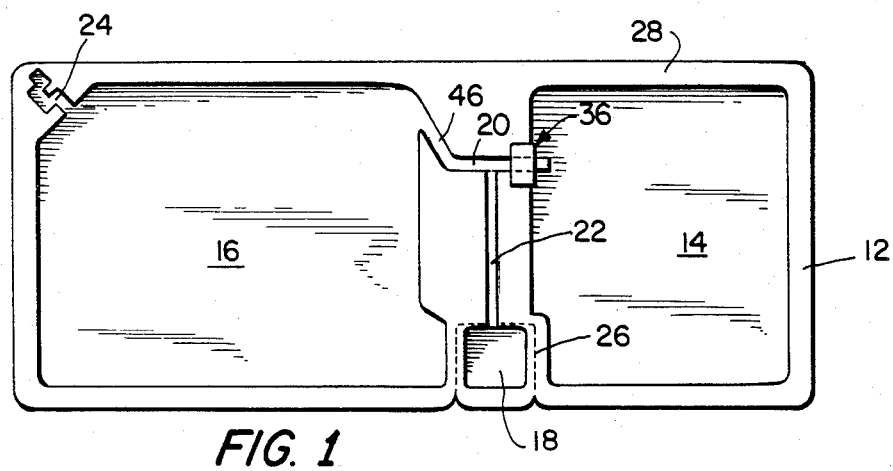
FIG. 1 is a top plan view of the specimen tray of the present invention.
Figure 2:
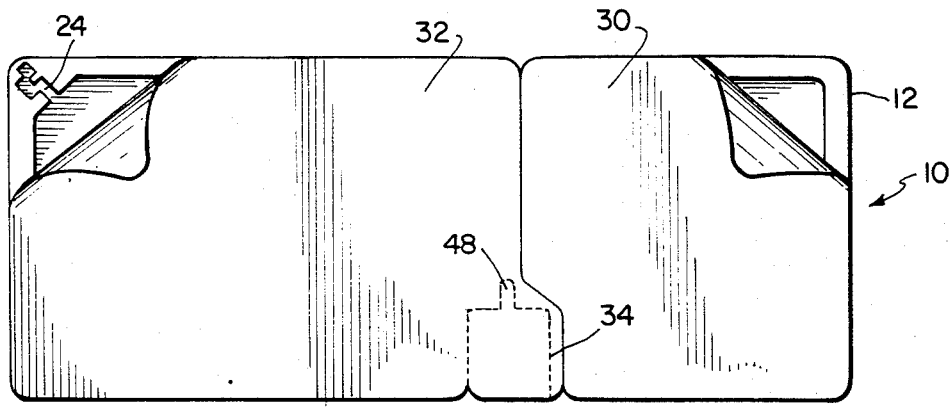
FIG. 2 is a top plan view of the covered specimen tray of the present invention.

FIGS. 1 and 2 show the specimen collection apparatus 10 of the present invention. Apparatus 10 includes an open tray 12 having a component storage compartment 14, a waste urine collection compartment 16, and a specimen compartment 18. A urine drainage canal 20 leads to the urine collection compartment 16, and a specimen canal 22 branches from the urine drainage canal and leads to the specimen collection compartment 18. Finally, a tortuous vent 24 leads from the waste urine collection compartment 16. The entire tray 12 can be formed in a single operation as a molded package or blister package. In the forming operation, a line of perforations 26 is formed around specimen collection compartment 18 so that this compartment can be removed from the tray 12 after a specimen has been collected.

A relatively wide flange 28 is formed around the entire perimeter of tray 12 and wide separation areas are formed between the compartments of the tray. In order to close the tray compartments, cover pieces 30 and 32 are attached to peripheral flange 28 in the areas between the compartments. Cover pieces 30 and 32 should be formed from a strong durable material with a sticky adhesive on one side. The sticky sides of cover pieces 30 and 32 are attached to the tray 12 so that each of the compartments 14, 16 and 18 forms a closed container with the associated cover material. Cover material 32 also includes perforations 34 which substantially align with perforations 26 so that the cover material portion over compartment 18 will be removed when compartment 18 is removed from the tray 12.

Figure 4:
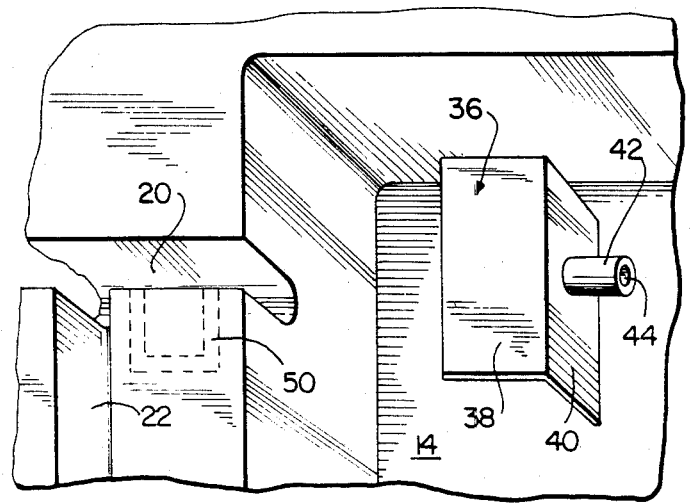
FIG. 4 is a part fragmentary perspective enlarged view showing the relationship between a catheter connector and a drainage canal of the present invention.

In order to connect drainage canal 22 to a catheter, catheter connector device 36 shown in FIGS. 1 and 4 is provided. Device 36 includes offset flanges 38 and 40 and a boss 42 having opening 44 which extends therethrough. Flanges 38 and 40 are attached to the top of tray 12 and to a side wall of compartment 14, respectively, so that opening 44 aligns with canal 20. A catheter can easily be slid onto boss 42 so that fluid passing through the catheter directly enters canal 20. Connector device 36 is supplied with the tray and attached as by gluing or the like to the tray prior to covering the tray with covering material 30 and 32. It should be understood that covering material 32 extends at least partially over flange 38 so that even if covering material 30 is completely removed, the entire area of canal 20 remains sealed to avoid leakage or contamination of the specimen passing through the canal.

When taking a urine sample, it is ofter desirable to avoid taking the sample from the initial discharge inasmuch this portion of the discharge contains debris and contamination which will produce an inaccurate urinalysis. The most desirable portion of the discharge for a specimen is in midstream. Accordingly a curved portion 46 is contained in canal 20 so that the resistance to flow in canal 20 can be altered. Curve 46 bends away from the position of compartment 18 so that with tray 12 flat, the discharge will pass by canal 22 and enter compartment 16 directly. However, during midstream flow, the tray 12 can be tilted upright so that compartment 18 is below canal 20 and the resistance to flow is increased by the upward turn 46 thus causing some of the discharge to flow downwardly through canal 22 into container 18 until the container is full. Then the tray can be laid flat again so that the remainder of discharge enters compartment 16.

Figure 3:
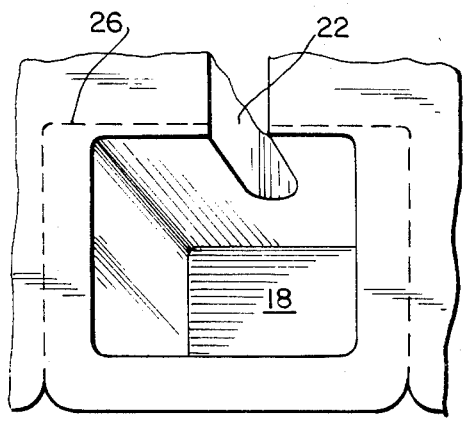
FIG. 3 is a part fragmentary perspective view of the specimen container of the present invention.

FIG. 3 shows specimen sampling compartment 18 in detail. As shown in FIG. 3, perforations 26 extend around the perimeter of compartment 18 so that it can be easily removed from tray 12. However, once removed, it is desirable to close off the area of channel 22 which enters compartment 18. For this purpose, the area of cover 32 with perforations is made to be slightly longer than compartment 18 and provided with a closure tab 48 which can be bent down over the area of canal 22 as it enters compartment 18. Accordingly, compartment 18 can be entirely sealed in this manner so that absolutely no leakage can occur from compartment 18 during transportation of the collected specimen.

In use, the apparatus is supplied with all of the necessary elements for taking a urine sample contained within compartment 14 and closed by cover member 30 to maintain these materials in an aseptic condition. These materials may include the catheter for connection to connector 36, gloves, pads, etc., all of which are well known implements for such a procedure. When taking the sample, cover member 30 is first removed from tray 12 and the necessary implements are removed from compartment 14. The catheter may already be connected to connector device 36 or may be contained in compartment 14 and attached to the connecting device. When the patient begins to discharge through the catheter, the tray 12 is maintained in a level position or compartment 18 may be raised slightly so that the initial portion of the discharge passes through canal 20 into compartment 16. After the first portion of the discharge has passed into compartment 16, the position of the tray 12 is changed so that compartment 18 is below canal 20. The urine then flows into compartment 18 due to the increased resistance of upward curved portion 46 of canal 20. When compartment 18 is filled, the tray may be again returned to the level position and drainage of the bladder can be completed into compartment 16. After the bladder has been drained completely, the catheter is removed and placed in storage area 14 with the used implements. The cover portion 30 may then be replaced on compartment 14. Compartment 18 is then removed along perforations 26 together with the cover member therefor which cover member is removed along perforations 34. The end of the cover member is then folded down and flap 48 is secured to completely enclose the sample in container 18. The sample is then secure for transportation to the area where urinalysis will be performed. The tray is removed to a disposal area where the remainder of the corner of cover material 32 is lifted as shown in FIG. 2 so that the wast urine may be disposed. The contents of compartment 16 can thus be poured out neatly with no spillage.

It can be seen that the apparatus of the present invention provides a system wherein a urine sample can be taken easily and the waste urine and used components disposed of neatly. All of the implements can be aseptically stored prior to use and disposed of after use in the same way. The entire apparatus operates neatly and efficiently to provide a contamination free urine sample which is sealed in its own container. The container 18 can be marked with the patients name for identification and then removed to a separate area for the urinalysis.

As an alternate to the use of connector device 36, a tortuous path such as that used in vent 24 can be included in canal 20 prior to the branch of canal 22. Such a tortutous path is shown in phatom at 50 in FIG. 4. This tortuous path inhibits the progression of bacteria to canal 22 and, thus, into the specimen taken at compartment 18. Accordingly, a simple plastic tube may be connected to canal 20 as by gluing or the like. In this case, a slight air leak into the front of canal 20 will not effect the quality of the specimen since the bacteria will be stopped by the tortuous path.

The foregoing description is provided for the purposes of illustrating the invention but is not considered to limit the scope thereof in any way. Clearly, numerous additions, modifications and other changes can be made to the present invention without departing from the scope thereof as set forth in appended claims.

What is claimed is:
1. A urine specimen collection apparatus comprising:
   a urine collection tray having a specimen inlet, a sample compartment, a storage compartment, a waste fluid compartment, and a canal connecting said inlet to said sample compartment and said waste fluid compartment;
   a covering disposed over said sample compartment, said waste fluid compartment, said storage compartment and said canal to close said compartments from ambient air;
   said closed storage compartment holding implements to be used during a catheterization procedure for taking a urine sample; and
   means defining a weakened line for separating said sample compartment from said tray;
   whereby said fluid sample may removed from said tray for urinalysis.
2. The apparatus of claim 1 wherein said canal includes a drainage canal connected from said inlet to said waste fluid compartment and a sample canal connected from said drainage canal to said sample compartment.
3. The apparatus of claim 1 wherein said covering comprises a flexible covering material disposed over said canal, said sample compartment and said waste fluid compartment.
4. The apparatus of claim 2 wherein said drainage canal includes a portion curved away from said sample compartment.
5. The apparatus of claim 1 including means to vary the resistance of flow through portions of said canal to direct the flow to either of said compartments.

6. The apparatus of claim 1 including a connector means attached to said inlet for attaching said inlet to a catheter.

7. A urine specimen collection apparatus comprising:
- a unitary one piece tray having a specimen inlet, a sample compartment, a waste urine compartment, a storage compartment and a canal connecting said inlet to said sample compartment and said waste urine compartment;
- said storage compartment holding implements for use during a catheterization procedure for taking a urine sample;
- a covering disposed over said sample compartment, said waste urine and storage compartments, and said canal to enclose said compartments; and
- means for removing said sample compartment from said tray, said means comprising a weakened line formed in said tray around said sample compartment and in said covering material around said sample compartment for separating said sample compartment from said tray.
- whereby a fluid sample may be taken and removed from said tray for processing.

8. The apparatus of claim 7 including a second removable covering disposed over said storage compartment.

* * * * *